(12) United States Patent
Tracy (10) Patent No.: US 9,320,641 B2
(45) Date of Patent: *Apr. 26, 2016

(54) ARTICULATING SPEAKER ASSEMBLY PROVIDING FOR PIVOTAL ADJUSTMENT OF CONNECTED FIRST AND SECOND MEMBERS

(71) Applicant: Dennis A Tracy, Culver City, CA (US)

(72) Inventor: Dennis A Tracy, Culver City, CA (US)

(*) Notice: Subject to any disclaimer, the term of this patent is extended or adjusted under 35 U.S.C. 154(b) by 357 days.

This patent is subject to a terminal disclaimer.

(21) Appl. No.: 13/949,398

(22) Filed: Jul. 24, 2013

(65) Prior Publication Data

US 2013/0308789 A1    Nov. 21, 2013

Related U.S. Application Data

(63) Continuation of application No. 13/187,997, filed on Jul. 21, 2011, now Pat. No. 8,526,662.

(60) Provisional application No. 61/344,490, filed on Aug. 5, 2010, provisional application No. 61/443,424, filed on Feb. 16, 2011.

(51) Int. Cl.
| | |
|---|---|
| *H04R 1/02* | (2006.01) |
| *A61F 6/14* | (2006.01) |
| *H04R 5/02* | (2006.01) |
| *B60R 11/02* | (2006.01) |

(52) U.S. Cl.
CPC ............. *A61F 6/142* (2013.01); *B60R 11/0217* (2013.01); *H04R 5/02* (2013.01)

(58) Field of Classification Search
CPC .......... H04R 1/02; H04R 1/025; H04R 1/026; H05R 5/02

USPC ................... 381/86, 345, 182, 186, 386–395; 181/198–199; 379/430

See application file for complete search history.

(56) References Cited

U.S. PATENT DOCUMENTS

| | | |
|---|---|---|
| 4,061,877 A | 12/1977 | Phillips |
| 4,182,429 A | 1/1980 | Senzaki |
| 4,199,657 A | 4/1980 | Lane |
| 4,597,470 A | 7/1986 | Takagi et al. |
| 4,757,544 A | 7/1988 | Guy |

(Continued)

FOREIGN PATENT DOCUMENTS

| | | |
|---|---|---|
| CN | 2114935 | 9/1992 |
| JP | 2005101988 | 4/2005 |

(Continued)

OTHER PUBLICATIONS

Hiraga, Jean: "Les Haut-Parleurs", Nov. 2, 2000, Dunod, Paris, SP002675504, ISBN: 2-10-005268-3, p. 382, Enceinte Jean-Marie Reynaud.

*Primary Examiner* — Ahmad F Matar
*Assistant Examiner* — Katherine Faley
(74) *Attorney, Agent, or Firm* — Welsh Flaxman & Gitler LLC (57) ABSTRACT

An articulating speaker assembly includes a first member including a first driver and a second member including second driver. The first member and the second member are pivotally connected for selectively changing the profile of the speaker assembly. A central housing member is pivotally connected to each of the first member and the second member, wherein the central housing member supports a third driver.

14 Claims, 8 Drawing Sheets

(56) References Cited

U.S. PATENT DOCUMENTS

| | | | |
|---|---|---|---|
| 4,811,406 A | 3/1989 | Kawachi | |
| 4,882,760 A | 11/1989 | Yee | |
| 4,932,060 A | 6/1990 | Schreiber | |
| 4,953,223 A | 8/1990 | Householder | |
| 5,512,714 A | 4/1996 | Fenton | |
| 5,677,669 A | 10/1997 | Walkley, IV et al. | |
| 5,682,434 A | 10/1997 | Boyden | |
| 5,802,194 A | 9/1998 | Yamagishi et al. | |
| 6,282,297 B1 | 8/2001 | Lin | |
| 6,356,640 B1 | 3/2002 | Lin | |
| 6,466,675 B1 | 10/2002 | Tracy | |
| 7,036,781 B1 | 5/2006 | Bothe | |
| 7,206,427 B2 | 4/2007 | Simidian, II et al. | |
| 7,415,124 B2 | 8/2008 | Colich | |
| 7,593,536 B2 | 9/2009 | Sung et al. | |
| 8,526,662 B2 * | 9/2013 | Tracy | 381/387 |
| 2001/0031061 A1 * | 10/2001 | Coombs et al. | 381/349 |
| 2002/0146140 A1 | 10/2002 | Chiu | |
| 2003/0026446 A1 | 2/2003 | Davis | |
| 2003/0076964 A1 | 4/2003 | Stickles et al. | |
| 2003/0231782 A1 | 12/2003 | Engebretson et al. | |
| 2007/0110267 A1 | 5/2007 | Liu | |
| 2008/0000714 A1 * | 1/2008 | Adams | 181/148 |
| 2008/0089537 A1 | 4/2008 | Scheel et al. | |
| 2008/0123894 A1 | 5/2008 | Lu | |
| 2008/0240487 A1 | 10/2008 | Lee | |
| 2008/0267429 A1 | 10/2008 | Tracy | |
| 2009/0279732 A1 | 11/2009 | Maurer et al. | |
| 2010/0046786 A1 | 2/2010 | Zhen | |
| 2010/0054522 A1 | 3/2010 | Maurer et al. | |
| 2010/0208913 A1 | 8/2010 | Budinger et al. | |

FOREIGN PATENT DOCUMENTS

| | | |
|---|---|---|
| KR | 20030076831 | 9/2003 |
| WO | WO 2007007083 | 1/2007 |

* cited by examiner

ARTICULATING SPEAKER ASSEMBLY PROVIDING FOR PIVOTAL ADJUSTMENT OF CONNECTED FIRST AND SECOND MEMBERS

CROSS REFERENCE TO RELATED APPLICATIONS

This application is a continuation of U.S. patent application Ser. No. 13/187,997, entitled "ARTICULATING SPEAKER ASSEMBLY PROVIDING FOR PIVOTAL ADJUSTMENT OF CONNECTED FIRST AND SECOND MEMBERS," filed Jul. 21, 2011, which is currently pending, which claims the benefit of U.S. Provisional Application Ser. Nos. 61/344,490, entitled 'SPEAKER ASSEMBLY', filed Aug. 5. 2010, and 61/443,424, entitled"ARTICULATING SPEAKER ASSEMBLY", filed Feb. 16, 2011.

BACKGROUND OF THE INVENTION

1. Field of the Invention

The invention relates to a speaker assembly. More particularly, the invention relates to an articulating speaker assembly for integration within a passenger service unit of an aircraft.

2. Description of the Related Art

The current global community has made it possible for people all around the country, and around the world, to interact for both business and personal reasons. For many people, this requires they spend considerable time traveling from one location to another location. More often than not, these people travel in aircraft. Whether these people travel in private or commercial aircraft, they desire high quality entertainment during the many hours they spend within the confines of an aircraft. However, while high quality entertainment, for example, digital video with CD quality sound, is readily available for theater and home use, the weight, size and available space requirements for use in aircraft make it very difficult to incorporate high fidelity systems within an aircraft. This problem is especially pronounced for audio loudspeaker assemblies when one attempts to meet the size, weight and shape requirements for use in aircrafts.

In the aircraft industry, great priority is placed upon component weight and size reduction. In addition, spacing and positioning of the loudspeaker assemblies are a great priority to those optimizing the operation of aircraft. The size, weight and shape of conventional terrestrial loudspeaker assembly designs adversely affect range and payload. These concerns are notable when one attempts to make changes within smaller, private jets. For example, a small increase in the weight carried by an aircraft results in a substantial increase in fuel consumption of the aircraft. In addition, the limited space available within an aircraft dictates the use of any space within the aircraft be carefully considered by those responsible for ensuring the comfort of passengers.

Lightweight and compact audio loudspeakers are currently available. These loudspeakers, however, substantially compromise sound quality for reductions in size and weight. An individual wishing to add an audio system to an aircraft must make a choice between high fidelity loudspeakers not suiting the size and weight requirements of the aircraft and lower quality loudspeakers providing desirable size and weight characteristics.

A need, therefore, exists for a loudspeaker assembly providing high fidelity sound, while meeting the size, weight and positioning profile requirements of an aircraft. The present invention provides such a loudspeaker assembly.

SUMMARY OF THE INVENTION

It is, therefore, an object of the present invention to provide an articulating speaker assembly including a first member having a first driver and a second member having a second driver. The first member and the second member are pivotally connected for selectively changing a profile of the articulating speaker assembly. A central housing member is pivotally connected to each of the first member and the second member, wherein the central housing member supports a third driver.

It is also an object of the present invention to provide an articulating speaker assembly wherein the first driver is a midrange driver and the second driver is a midrange driver.

It is another object of the present invention to provide an articulating speaker assembly wherein the third driver is a high frequency driver.

It is a further object of the present invention to provide an articulating speaker assembly wherein the first member includes a first cylindrical enclosure defining a cavity shaped and dimensioned for receiving the first driver secured within the first cylindrical enclosure, and the second member includes a second cylindrical enclosure defining a cavity shaped and dimensioned for receiving the second driver secured within the second cylindrical enclosure.

It is also an object of the present invention to provide an articulating speaker assembly wherein the first member includes a first connection arm pivotally coupled to the central housing member and the second member includes a second connection arm pivotally coupled to the central housing member.

It is another object of the present invention to provide an articulating speaker assembly wherein the first connection arm includes a first coupling cylinder secured at a distal end of the first connection arm opposite the first driver, and the second connection arm includes a second coupling cylinder secured at a distal end of the second connection arm opposite the second driver.

It is another object of the present invention to provide an articulating speaker assembly wherein the first coupling cylinder is oriented transverse to the first connection arm and is shaped and dimensioned to fit within the central housing member along a first end thereof, and the second coupling cylinder is oriented transverse to the second connection arm and is shaped and dimensioned to fit within the central housing member along a second end thereof.

It is a further object of the present invention to provide an articulating speaker assembly wherein the central housing member is provided with a first arcuate slot through which the first connection arm passes, the first arcuate slot limiting pivotal movement of the first member relative to the central housing member, and the central housing member is provided with a second arcuate slot through which the second connection arm passes, the second arcuate slot limiting pivotal movement of the second member relative to the central housing member.

It is also an object of the present invention to provide an articulating speaker assembly wherein the central housing member includes a central aperture shaped and dimensioned for receiving the third driver.

It is another object of the present invention to provide an articulating speaker assembly including a first midrange member including a first midrange driver and a central housing member pivotally connected to the first midrange member, the central housing member supporting a driver.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

Figure 1:
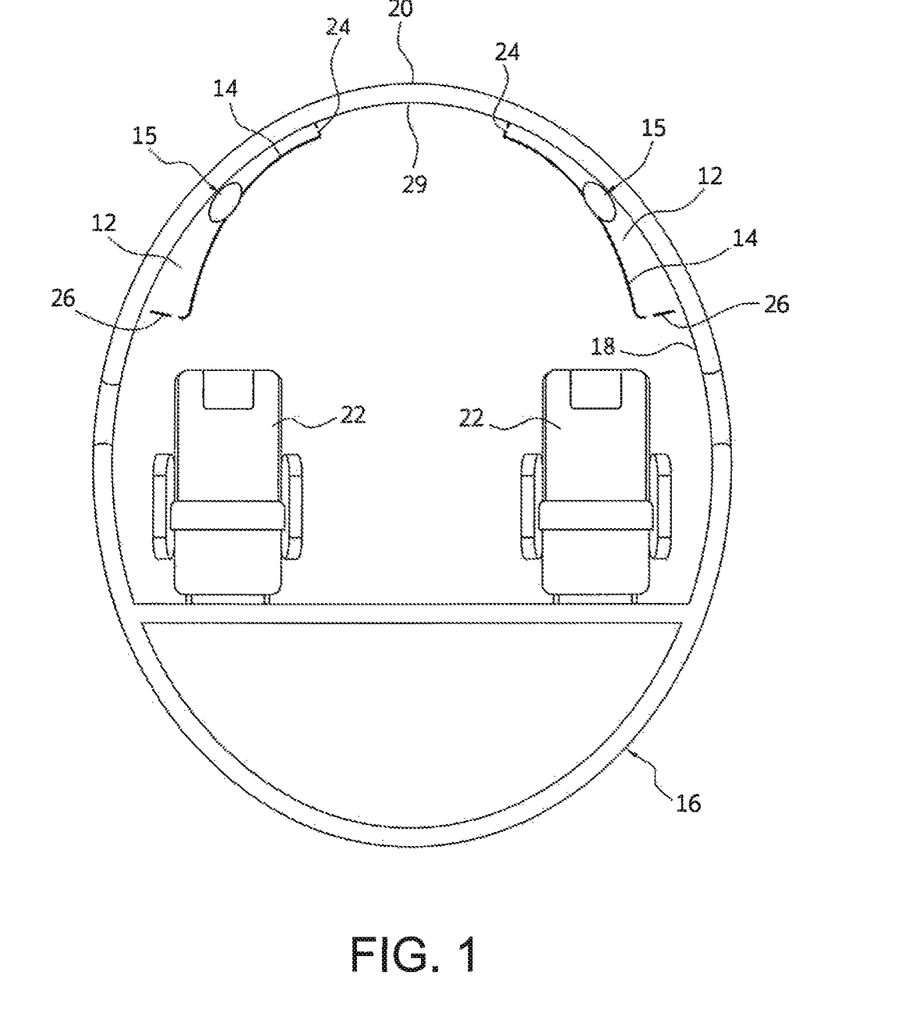
FIG. 1 is a cross sectional schematic of an aircraft fuselage with the present speaker assembly installed.

In accordance with the present invention, and with reference to FIG. 1, a small profile articulating speaker assembly 15 shaped and dimensioned for positioning within an internal cavity 12 of a passenger service unit 14 of an aircraft 16 is disclosed.

As will be appreciated by those skilled in the art, a passenger service unit 14 is a structural element of an aircraft 16 in which those accessories providing for passenger comfort and service are positioned. The passenger service unit 14 is commonly positioned along the interior wall 18 of the aircraft fuselage 20 above the side window and directly above the passenger seat 22 allowing for direct access by passengers sitting in the seats adjacent thereto. The passenger service unit 14 commonly houses air flow devices (for example, an aircraft gasper), lights, public address speakers, messaging buttons for contacting the flight attendants, and various warning lights. In addition, and in accordance with many aircraft designs, the lateral edges 24, 26 of the passenger service unit 14 allow for creation and transmission of up-wash light and down-wash light. Depending upon the specific aircraft and the custom interior design thereof, the passenger service unit may take a variety of shapes. In fact, most passenger service units exhibit different and changing profiles along their length and width.

In particular, the passenger service unit 14 extends along the longitudinal axis of the aircraft 16 from the aft of the aircraft 16 to the fore of the aircraft 16. In accordance with the present invention, the passenger service unit 14 is provided with an internal cavity 12 through which light, electrical wires and other functional components are run along the length of the aircraft 16. In accordance with a preferred embodiment of the present invention, a plurality of speaker assemblies 15 are positioned within the internal cavity 12 at locations along the length of the aircraft 16. The articulating speaker assembly 15 described below allows for ready adjustment so the speaker assembly 15 may be fit within different locations without entirely redesigning the speaker assembly. That is, different locations along a passenger service unit 14, as well as different passenger services units, will have different curvatures and shapes necessitating changes in the shape of a speaker mounted therein. In addition, articulation of the speaker assembly 15 allows for changes in the shape of a grill improving aesthetics and controlling crossovers.

In accordance with a preferred embodiment, the speaker assembly 15 incorporates a variety of features which reduce the size and weight of the speaker assembly, allowing for positioning at various locations within the internal cavity 12 of the passenger service unit 14 by simply adjusting the orientation of the speaker assembly 15 without compromising the integrity of the sound generated by the speaker assembly 15.

The speaker assembly 15 includes first and second midrange members 35, 55 pivotally connected for selectively changing the profile of the speaker assembly 15 and allowing for positioning within a variety of envelopes or available spaces within an aircraft 16, in particular, within the passenger service unit 14 of the aircraft. The first and second midrange members 35, 55 are substantially mirror images of each other and are pivotally connected to a central high frequency housing member 25 within which a high frequency driver (or third driver) 28 is mounted.

With reference to the first midrange member 35, it includes a first cylindrical enclosure 30 with a first base wall 32 and a substantially circular first sidewall 34. The first cylindrical enclosure 30 defines a cavity 36 shaped and dimensioned for receiving a first midrange driver for first driver) 38. The first midrange driver 38 is secured within the first cylindrical enclosure 30 via a first face plate 40.

The first face plate 40 includes a top surface 42 and a bottom surface 44. The first face plate 40 also includes a first midrange aperture 46. The first midrange driver 38 is secured to the first face plate 40 using conventional adhesive and the first face plate 40 is then secured to the first cylindrical enclosure 30 using screws 48 with the first midrange driver 38 positioned within the cavity 36 defined by the first cylindrical enclosure 30.

With reference to second midrange member 55, it includes a second cylindrical enclosure 50 with a second base wall 52 and substantially circular second side all 54. The second cylindrical enclosure 50 defines a cavity 56 shaped and dimensioned for receiving a second midrange driver (or second driver) 58. The second midrange driver 58 is secured within the second cylindrical enclosure 50 via a second face plate 60.

The second face plate 60 includes a second midrange aperture 62. The second midrange driver 58 is secured to the second face plate 60 using conventional adhesive and the second face plate 60 is then secured to the second cylindrical enclosure 50 using screws 64 with the second midrange driver 58 positioned within the cavity 65 defined by the second cylindrical enclosure 50.

Figure 2:
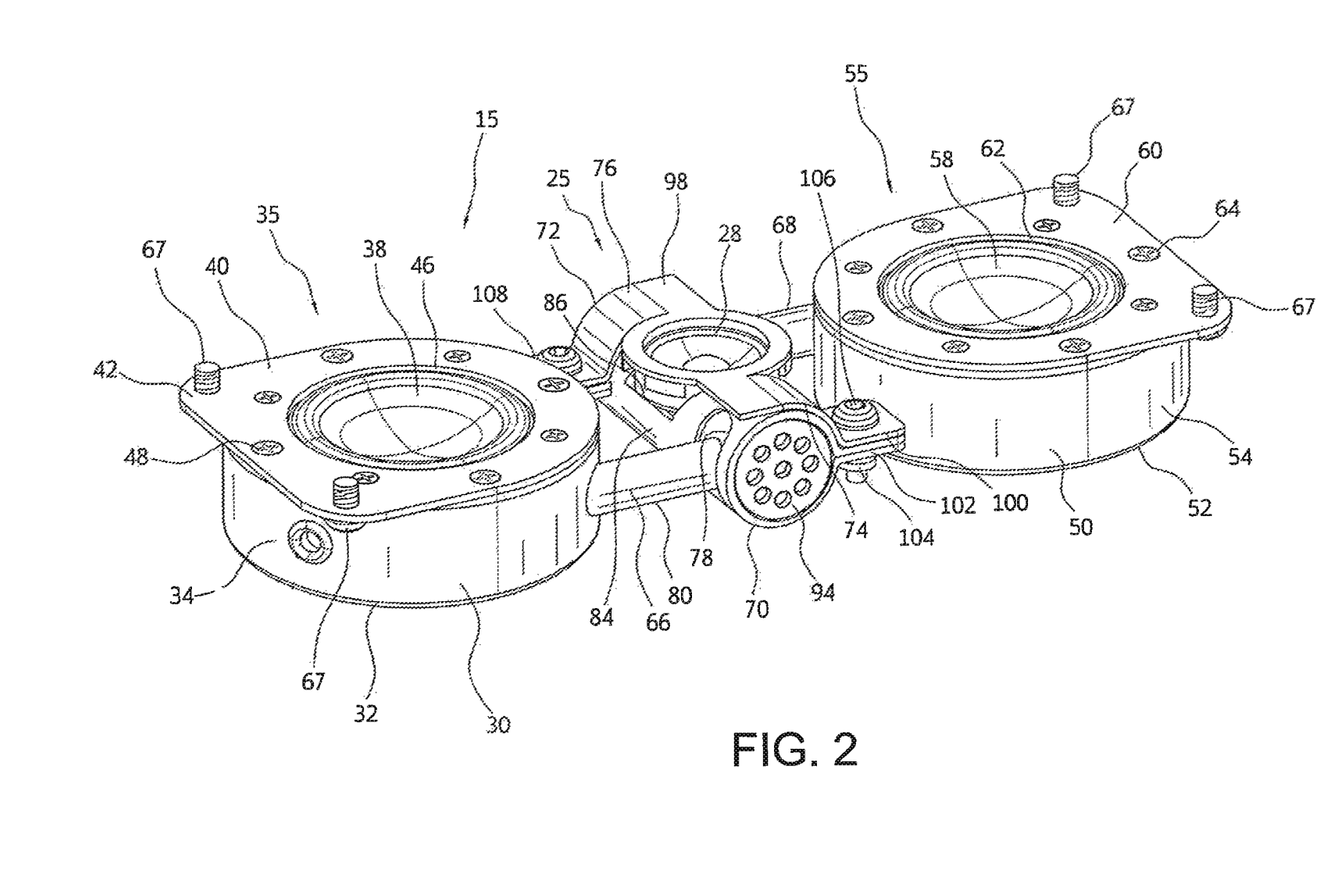
FIG. 2 is a perspective view of a speaker assembly in accordance with a first embodiment.
Figure 3:
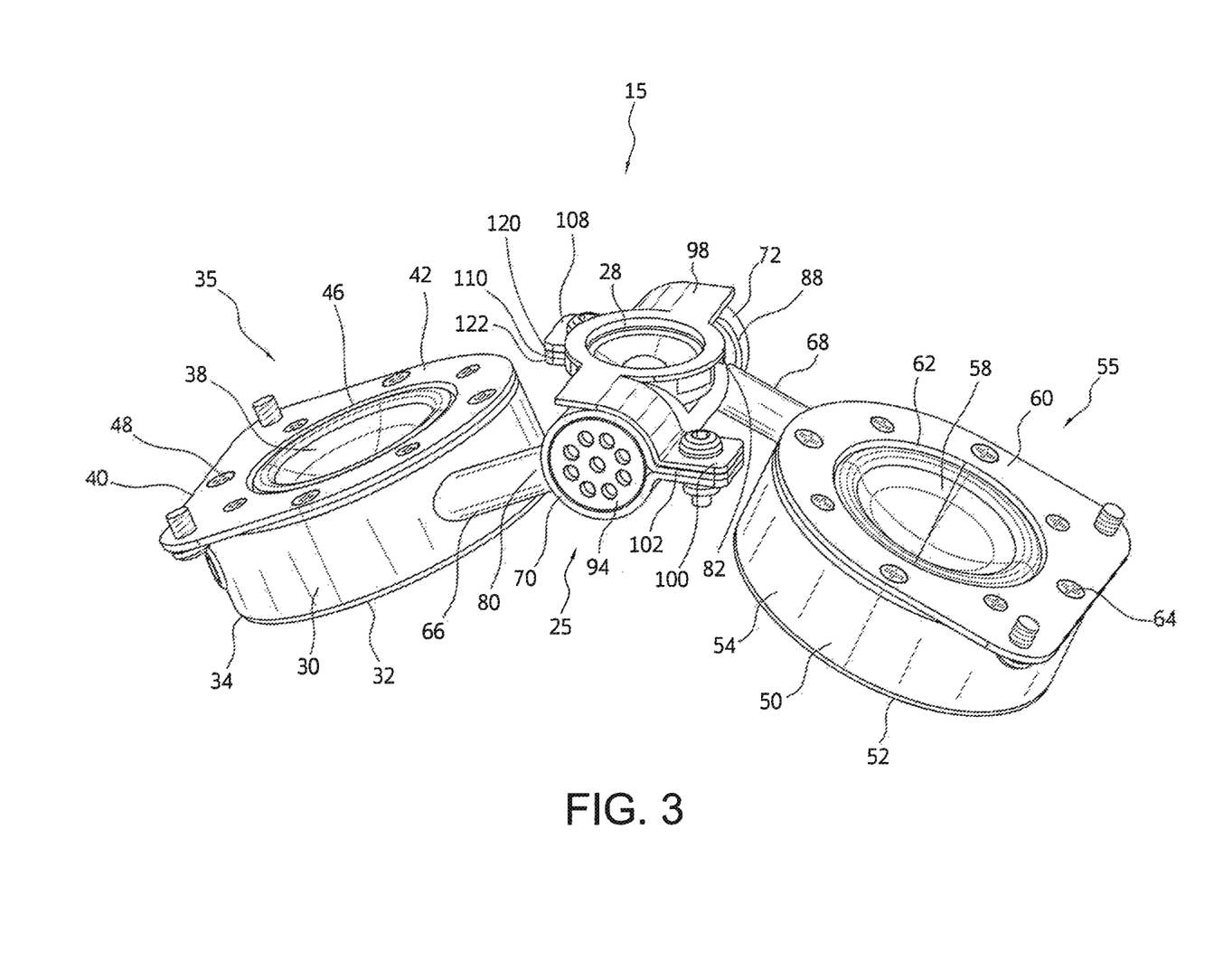
FIGS. 3 to 11 are views of the speaker assembly shown in FIG. 2 in various orientations and from various viewpoints (FIGS. 5-11 showing the speaker assembly without the nylon perforated end caps of the high frequency housing member installed).
Figure 4:
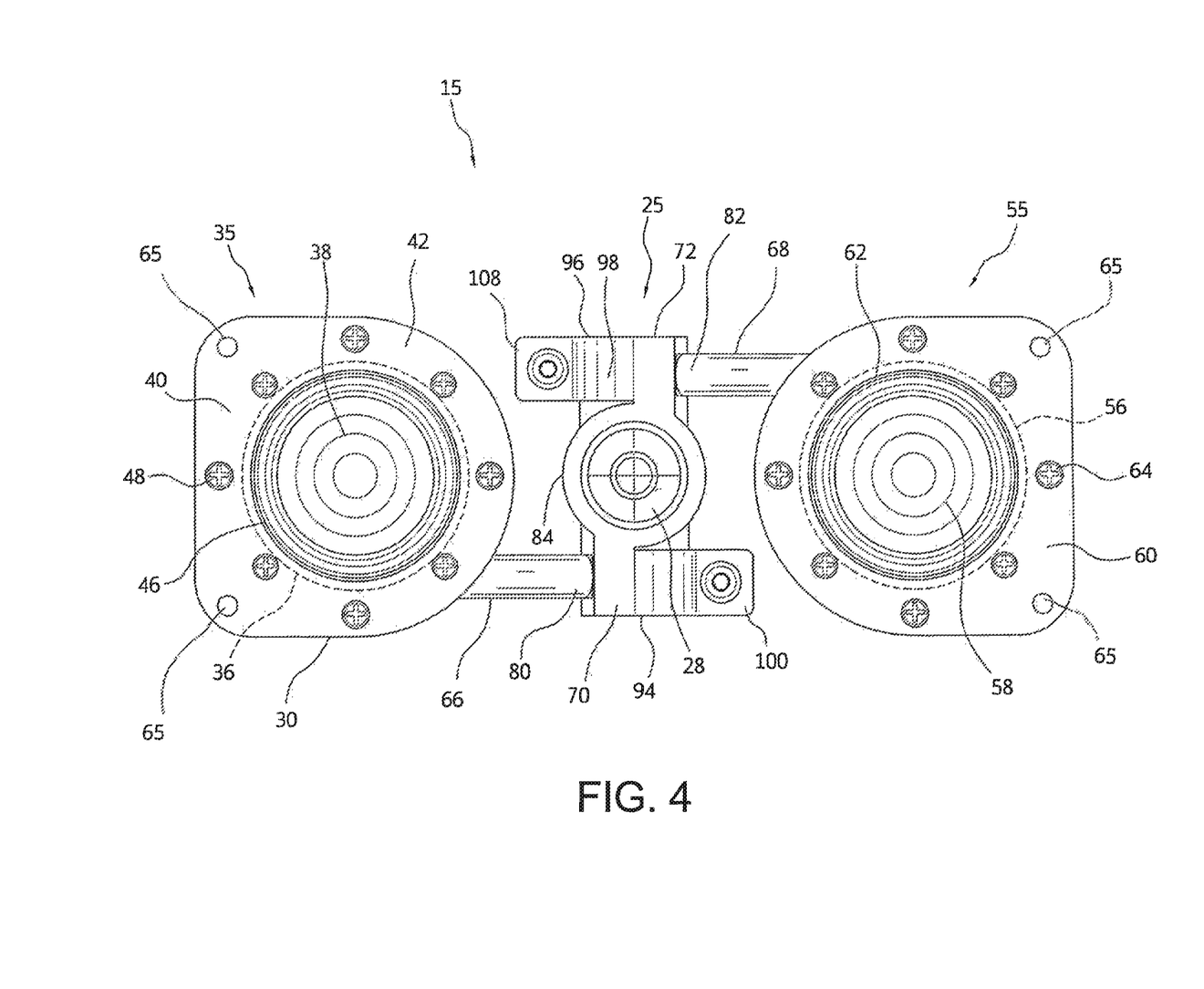
Figure 5:
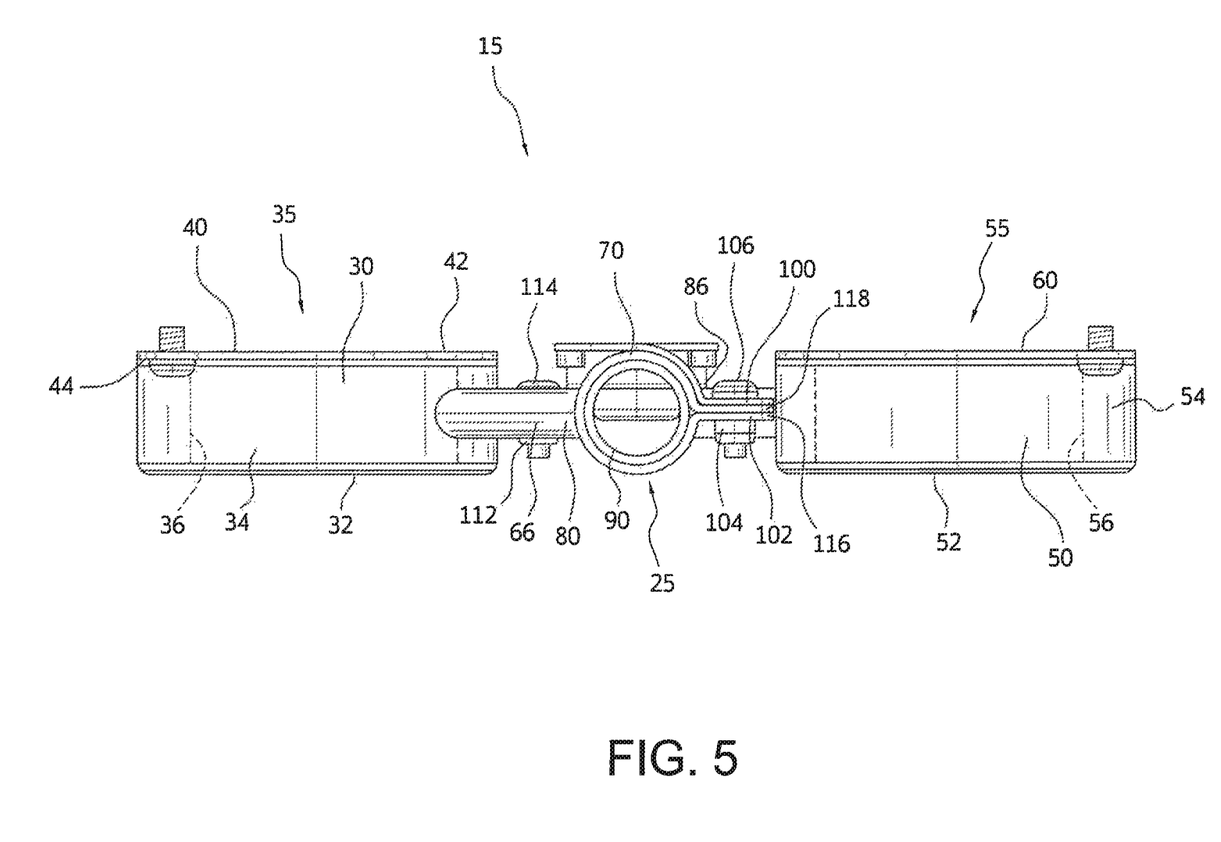
Figures 6, 7:
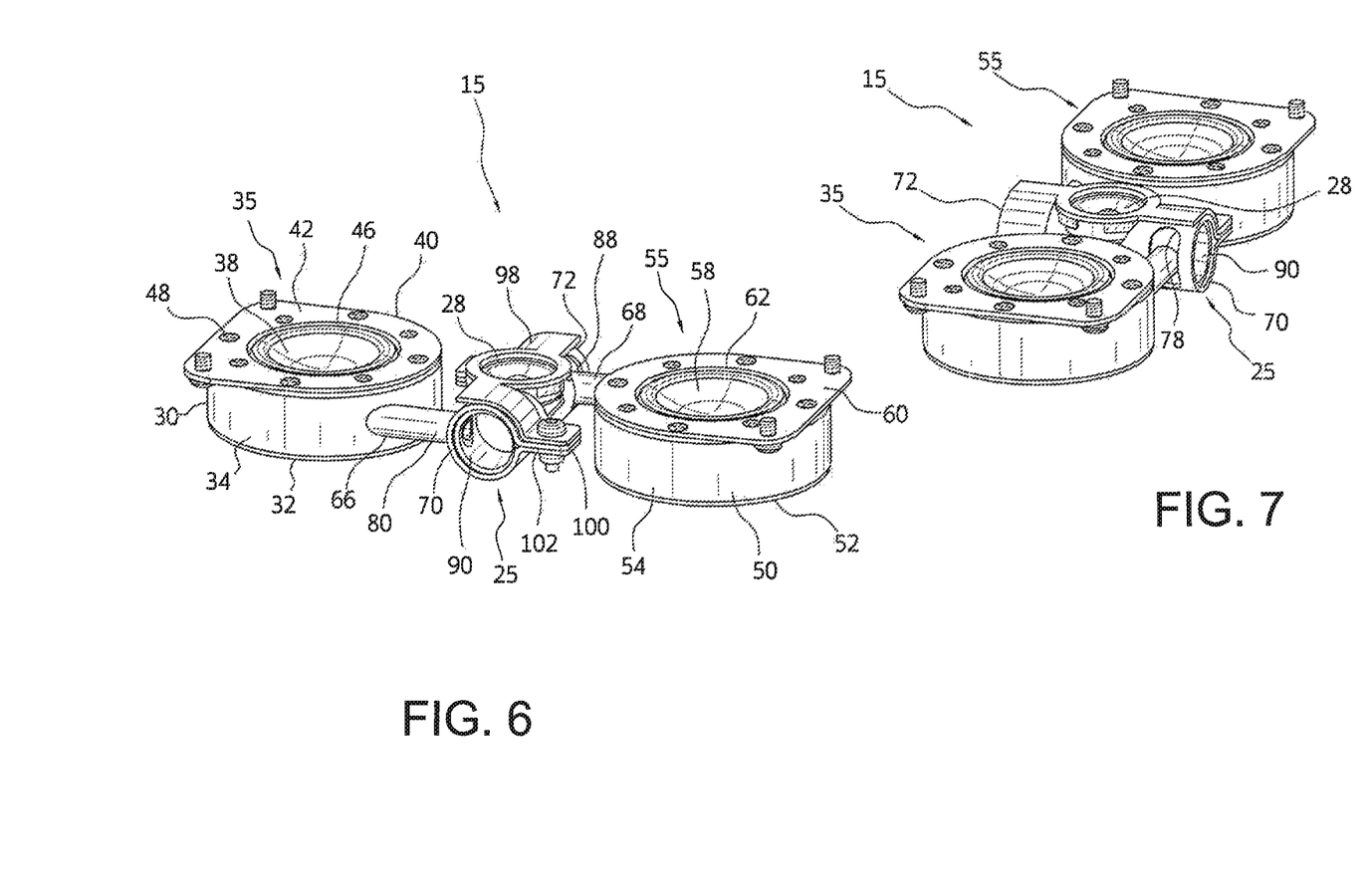
Figures 8, 9:
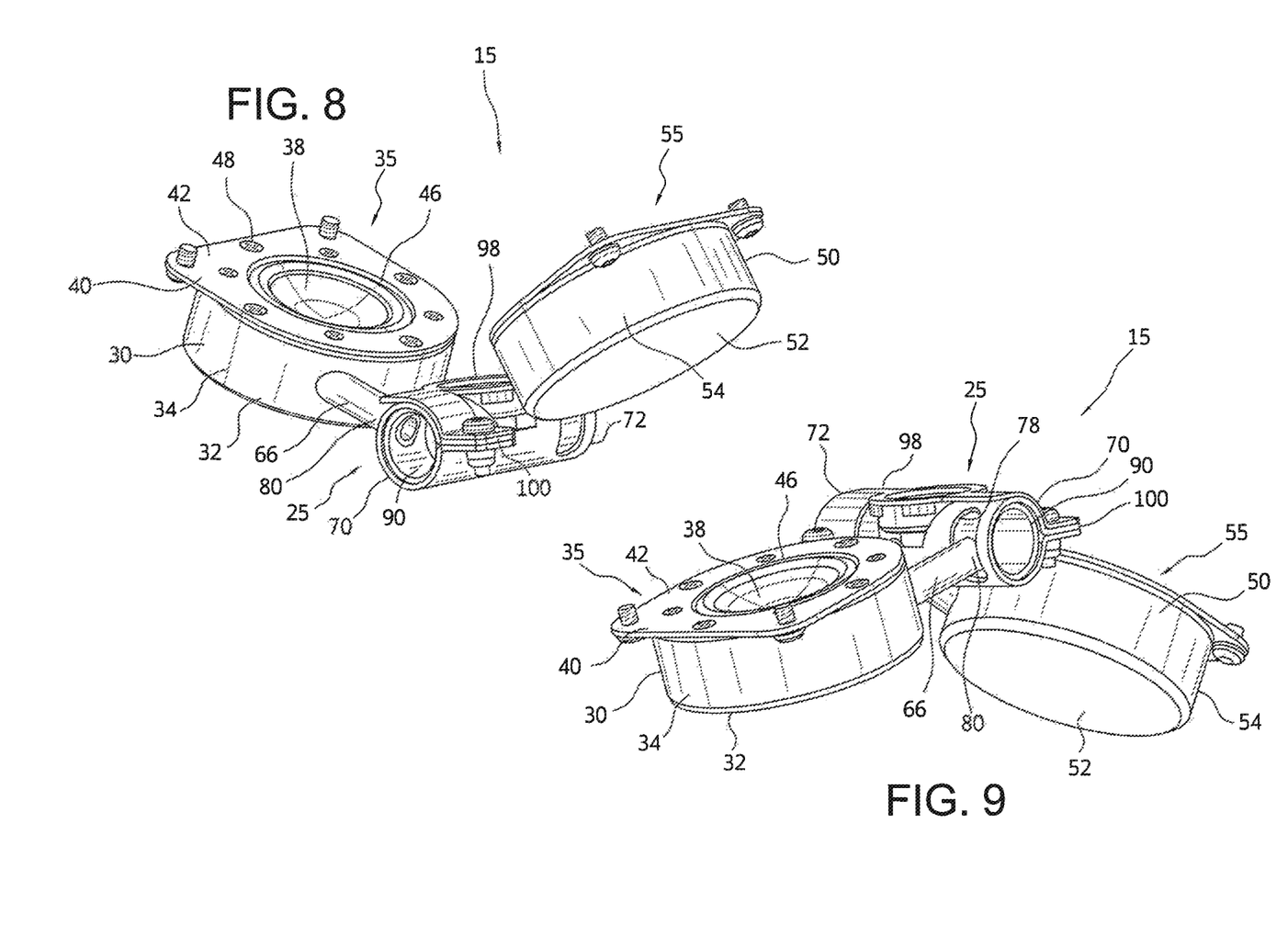
Figure 10:
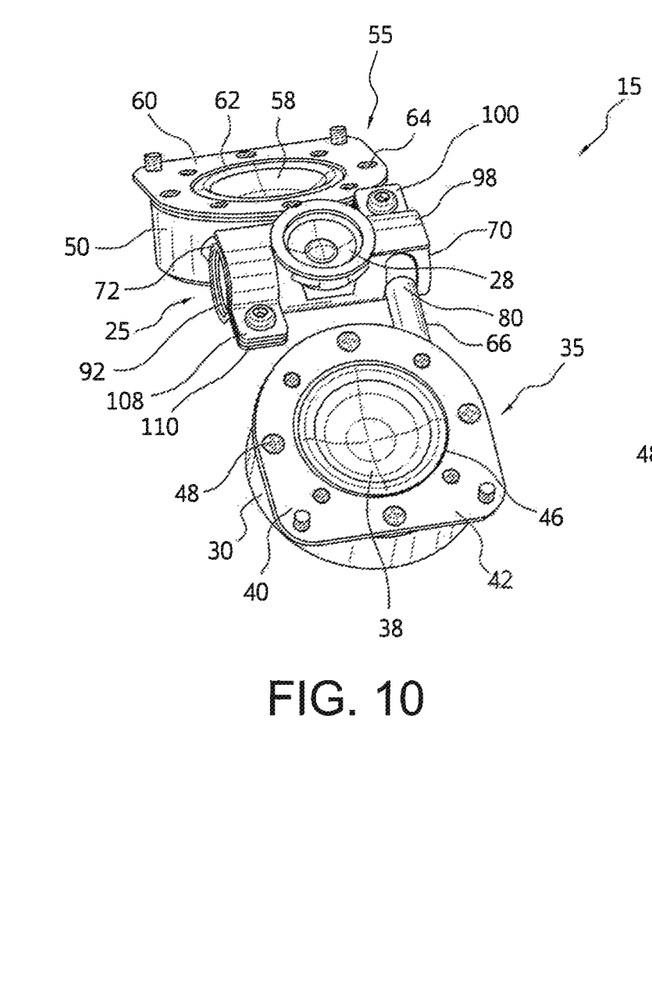
Figure 11:
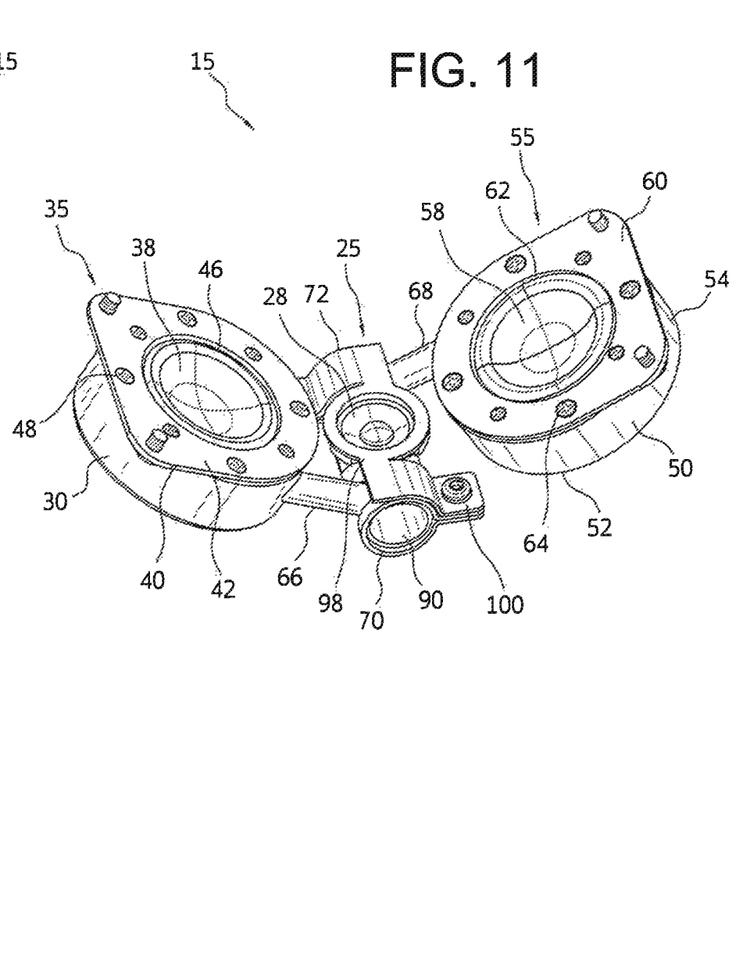

Referring to FIG. 2, each of the first and second midrange members 35, 55 includes mounting apertures 65 (as best shown in FIG. 4) for attachment to supporting structures within the aircraft using screw 67 (as best shown in FIG. 2), for example. In this way, the articulating structure of the speaker assembly 15 does not have to support the weight of the speaker assembly 15.

Connecting the first and second midrange members 35, 55 is the central high frequency housing member 25. As such, each of the first and second midrange members 35, 55 includes a connection arm 66, 68. The first connection arm 66 of the first midrange member 35 is pivotally coupled to the central high frequency housing member 25 along a first side 70 thereof, while the second connection arm 68 of the second midrange member 55 is pivotally coupled to the central high frequency housing member 25 along an opposite second side 72 thereof.

More particularly, the first connection arm 66 includes a first coupling cylinder 90 secured at the distal end thereof opposite the first midrange driver 38. The first coupling cylinder 90 is oriented transverse to the connection arm 66 (that is, the central radial axis of the coupling cylinder 90 is substantially perpendicular to the central radial axis of the connection arm 66) and is shaped and dimensioned to fit within the central high frequency housing member 25 along the first side 70 thereof. The first coupling cylinder 90 is shaped and dimensioned to snuggly fit within the central high frequency housing member 25 such that upon tightening of the central high frequency housing member 25 in a manner discussed below in greater detail, the first coupling cylinder 90 and, ultimately, the first midrange member 35 are frictionally locked in a desired orientation relative to the central high frequency housing member 25.

In positioning the first coupling cylinder 90 within the central high frequency housing member 25, the central high frequency housing member 25 is provided with a first arcuate slot 78 through which the connection arm 66 passes as the coupling cylinder 90 sits within the housing member 25. In addition to providing a passageway for securing the first coupling cylinder 90 within the central high frequency housing member 25, the first arcuate slot 78 limits the pivotal movement of the first midrange member 35 relative to the central high frequency housing member 25. In accordance with a preferred embodiment, movement is limited to an arc of 32.5°.

The second midrange member 55 is similarly coupled to the central high frequency housing member 25. In particular, the second connection arm 68 includes a second coupling cylinder 92 secured at the distal end thereof opposite the second midrange driver 58. The second coupling cylinder 92 is oriented transversely to the connection arm 68 (that is, the radial axis of the second coupling cylinder 92 is substantially perpendicular to the radial axis of the connection arm 68) and is shaped and dimensioned to fit within the central high frequency housing member 25 along the second side 72 thereof. The second coupling cylinder 92 is shaped and dimensioned to snuggly fit within the central high frequency housing member 25 such that upon tightening of the central high frequency housing member 25 in a manner discussed below in greater detail, the second coupling cylinder 92 and, ultimately, the second midrange member 55 are frictionally locked in a desired orientation relative to the central high frequency housing member 25.

In positioning the second coupling cylinder 92 within the central high frequency housing member 25, the central high frequency housing member 25 is provided with a second arcuate slot 88 through which the connection arm 68 passes as the second coupling cylinder 92 sits within the high frequency housing member 25. In addition to providing a passageway for securing the second coupling cylinder 92 within, the central high frequency housing member 25, the second arcuate slot 88 limits the pivotal movement of the second midrange member 55 relative to the central high frequency housing member 25. In accordance with a preferred embodiment, movement is limited to an arc of 32.5°.

The first and second connection arms 66, 68, as well as the first and second coupling cylinders 90, 92, of the first and second midrange members 35, 55 are hollow tubular members that are in fluid communication (that is, permitting the transmission of sound therethrough) with the respective cavities 36, 56 of the first and second midrange members 35, 55 thereby effectively expanding the size of the cavities 36, 56 and enhancing the acoustic characteristics thereof. As such, the first and second ends 74, 76 of the central high frequency housing member 25 are provided with nylon perforated end caps 94, 96 allowing for controlled air flow between the respective cavities 36, 56, of the first and second midrange members 35, 55 and the environment external to the present speaker assembly 15. The speaker assembly 15 is shaped such that, even when mounted, space exists allowing for the flow of air through the end caps 94, 96.

It is contemplated the first and second coupling cylinders may be wrapped in foam to improve both the frictional locking and acoustic characteristics of the loudspeaker.

The central high frequency housing member 25 is substantially cylindrical and includes a first end 74 and a second end 76. Along the first end 74 thereof, the central high frequency housing member 25 includes the circumferential arcuate slot 78 in which the free end 80 of the first connection arm 66 of the first midrange member 35 is housed for pivotal movement relative to the central high frequency housing member 25. At the second end 76 of the central high frequency housing member 25, the circumferential arcuate slot 88 is formed in which the free end 82 of the second connection arm 68 of the second midrange member 55 is housed for pivotal movement relative to the central high frequency housing member 25.

The center 84 of the central high frequency housing member 25 includes a central aperture 86 shaped and dimensioned for receiving the high frequency driver 28. As shown in the attached figures, the central aperture 86 is centrally located relative to the circumferential first and second arcuate slots 78, 88 for the first and second connection arms 66, 68 maintaining the symmetry of the present speaker assembly 15.

The high frequency driver 28 is supported within the central aperture 86 by a mounting bracket 98 extending in a substantially S-shaped configuration from the first end 74 of the central high frequency housing member 25 to the second end 76 of the central high frequency housing member 25. The mounting bracket 98 includes a first tab 100 secured to a first mounting tab 102 at the first end 74 of the central high frequency housing member 25 by a nut 104 and bolt 106 and the mounting bracket 98 includes a second tab 108 secured to a second mounting tab 110 at the second end 76 of the central high frequency housing member 25 by a nut 112 and bolt 114.

The interaction of the nut 104 and bolt 106 with the first mounting tab 102 at the first end 74 of the central high frequency housing member 25 also serves a second purpose by allowing for selective tightening of the first coupling cylinder 90 held within the central high frequency housing member 25. In particular, the first end 74 of the central high frequency housing member 25 is formed as a split cylinder with first and second end members 116, 118 extending outwardly to form the first mounting tab 102. As such, by drawing these first and second end members 116, 118 toward each other under the control of the nut 104 and bolt 106 it is possible to slightly reduce the internal diameter of the central high frequency housing member 25 sufficiently to create frictional resistance to the movement of the first coupling cylinder 90.

Similarly, and with reference to the second end 76 of the central high frequency housing member 25, the interaction of the nut 112 and bolt 114 with the second mounting tab 110 at the second end 76 of the central high frequency housing member 25 serves a second purpose by allowing for selective tightening of the second coupling cylinder 92 held within the central high frequency housing member 25. In particular, the second end 76 of the central high frequency housing member 25 is formed as a split cylinder with first and second end members 120, 122 extending outwardly to form the second mounting tab 110. As such, by drawing these first and second end members 120, 122 toward each other under the control of the nut 112 and bolt 114 it is possible to slightly reduce the internal diameter of the central high frequency housing member 25 sufficiently to create frictional resistance to the movement of the second coupling cylinder 92.

It will be appreciated that although wiring diagrams are not disclosed herein, the present speaker assembly 15 is wired in a conventional manner.

Installation of either of the speaker assemblies 15 is completed by mounting the speaker assembly 15 at a desired location within the internal cavity of the passenger service unit 14. However, and although mounting within the passenger service unit 14 is contemplated in accordance with the present invention, it is appreciated the speaker assemblies may be mounted at various locations.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. An articulating speaker assembly for integration within a passenger compartment, comprising:
    a first member including a first speaker driver for generating sound, the first member includes a first enclosure defining a cavity, and a second member including a second speaker driver for generating sound, the second member includes a second enclosure defining a cavity, the first member and the second member pivotally connected for selectively changing a profile of the articulating speaker assembly;
    a central housing member pivotally connected to each of the first member and the second member, wherein the central housing member supports a third speaker driver for generating sound;
    wherein the first member includes a hollow tubular first connection arm extending from the first enclosure such that first connection arm is in fluid communication with the cavity defined by the first enclosure, the first connection arm being pivotally coupled to the central housing member, and the second member includes a hollow tubular second connection arm extending from the second enclosure such that first connection arm is in fluid communication with the cavity defined by the first enclosure, the second connection arm being pivotally coupled to the central housing member;
    wherein the first connection arm includes a first coupling cylinder secured at a distal end of the first connection arm opposite the first driver, and the second connection arm includes a second coupling cylinder secured at a distal end of the second connection arm opposite the second driver.

2. The articulating speaker assembly according to claim 1, wherein the first coupling cylinder is oriented transverse to the first connection arm and is shaped and dimensioned to fit within the central housing member along a first end thereof, and the second coupling cylinder is oriented transverse to the second connection arm and is shaped and dimensioned to fit within the central housing member along a second end thereof.

3. The articulating speaker assembly according to claim 2, wherein the central housing member is provided with a first arcuate slot through which the first connection arm passes, the first arcuate slot limiting pivotal movement of the first member relative to the central housing member, and the central housing member is provided with a second arcuate slot through which the second connection arm passes, the second arcuate slot limiting pivotal movement of the second member relative to the central housing member.

4. The articulating speaker assembly according to claim 1, wherein the first speaker driver is a midrange driver and the second speaker driver is a midrange driver.

5. The articulating speaker assembly according to claim 4, wherein the third speaker driver is a high frequency driver.

6. The articulating speaker assembly according to claim 1, wherein the first enclosure is a cylindrical enclosure and the second enclosure is a cylindrical enclosure.

7. The articulating speaker assembly according to claim 1, wherein the central housing member includes a central aperture shaped and dimensioned for receiving the third speaker driver.

8. An articulating speaker assembly for integration within a passenger compartment, comprising:
    a first member including a first speaker driver for generating sound, the first member includes a first enclosure defining a cavity, and a second member including a second speaker driver for generating sound, the second member includes a second enclosure defining a cavity, the first member and the second member pivotally connected for selectively changing a profile of the articulating speaker assembly;
    a central housing member pivotally connected to each of the first member and the second member, wherein the central housing member supports a third speaker driver for generating sound;
    the first member includes a first connection arm extending from the first enclosure, the first connection arm being pivotally coupled to the central housing member, and the second member includes a second connection arm extending from the second enclosure, the second connection arm being pivotally coupled to the central housing member; and
    the central housing member is provided with a first arcuate slot through which the first connection arm passes, the first arcuate slot limiting pivotal movement of the first member relative to the central housing member, and the central housing member is provided with a second arcuate slot through which the second connection arm passes, the second arcuate slot limiting pivotal movement of the second member relative to the central housing member.

9. The articulating speaker assembly according to claim 8, wherein the first speaker driver is a midrange driver and the second speaker driver is a midrange driver.

10. The articulating speaker assembly according to claim 9, wherein the third speaker driver is a high frequency driver.

11. The articulating speaker assembly according to claim 8, wherein the first enclosure is a cylindrical and the second enclosure is a cylindrical enclosure.

12. The articulating speaker assembly according to claim 8, wherein the first connection arm includes a first coupling cylinder secured at a distal end of the first connection arm opposite the first driver, and the second connection arm includes a second coupling cylinder secured at a distal end of the second connection arm opposite the second driver.

13. The articulating speaker assembly according to claim 12, wherein the first coupling cylinder is oriented transverse to the first connection arm and is shaped and dimensioned to fit within the central housing member along a first end thereof, and the second coupling cylinder is oriented transverse to the second connection arm and is shaped and dimensioned to fit within the central housing member along a second end thereof.

14. The articulating speaker assembly according to claim 8, wherein the central housing member includes a central aperture shaped and dimensioned for receiving the third speaker driver.

* * * * *